United States Patent [19]

LeVeen

[11] 4,230,129
[45] Oct. 28, 1980

[54] RADIO FREQUENCY, ELECTROMAGNETIC RADIATION DEVICE HAVING ORBITAL MOUNT

[76] Inventor: Harry H. LeVeen, 800 Poly Pl., Brooklyn, N.Y. 11209

[21] Appl. No.: 679,431

[22] Filed: Apr. 22, 1976

Related U.S. Application Data

[63] Continuation-in-part of Ser. No. 643,661, Dec. 23, 1975, Pat. No. 3,991,770, which is a continuation-in-part of Ser. No. 595,094, Jul. 11, 1975, abandoned, which is a continuation-in-part of Ser. No. 436,102, Jan. 24, 1974, abandoned.

[51] Int. Cl.³ .............................................. A61N 1/40
[52] U.S. Cl. ..................................... 128/804; 250/369
[58] Field of Search .......... 128/413, 404, 422, 1.3–1.5, 128/24 A, 804; 250/369; 219/10.57

[56] References Cited

U.S. PATENT DOCUMENTS

| | | | |
|---|---|---|---|
| 2,223,447 | 12/1940 | Hathaway | 128/413 |
| 3,237,623 | 3/1966 | Gordon | 128/24 A |
| 3,839,641 | 10/1974 | Cooke | 250/369 |
| 3,915,151 | 10/1975 | Kraus | 128/1.5 |

FOREIGN PATENT DOCUMENTS

| | | | |
|---|---|---|---|
| 917320 | 12/1972 | Canada | 128/404 |
| 32302 | 3/1934 | Netherlands | 128/413 |
| 618179 | 2/1949 | United Kingdom | 128/413 |
| 1045546 | 10/1966 | United Kingdom | 128/404 |

OTHER PUBLICATIONS

Goldenberg et al., "Direct . . . Local Hyperthermic", Zeitschrift fur Natur Forschuns, 8, 26, Apr. 1971, pp. 359–361.
Schonander Pamphlet, Feb. 1940, Sweden, pp. 1–8.

*Primary Examiner*—Lee S. Cohen
*Attorney, Agent, or Firm*—Brooks, Haidt, Haffner & Delahunty

[57] ABSTRACT

A method and apparatus for treating tumors, both benign and malignant, involving radio frequency heating of the tumor within the body of the animal host, the method comprising precisely locating and monitoring the tumor to be treated and so positioning radio frequency apparatus that sufficient energy is absorbed therefrom by the tumor for a period of time and with intensity sufficient to cause necrosis of said tumor, but without substantially affecting the tissues surrounding said tumor. The preferred apparatus is adapted for connecting the radio frequency treatment equipment to the output of a body scanner or the like such that the exact position and configuration of the tumor can be plotted in terms of rectangular coordinates and the radio frequency equipment can then be directed or focused precisely on the tumor location. Moreover, to avoid excessive heating or thermal damage to the surrounding tissue, the applicator plates or discs are moved in an orbital manner such that the tumor always lies on the axis between the applicator plates, and the radio frequency energy is concentrated therein. However, by dint of the orbital movement of the applicators, the energy is not continuously being applied to a confined area, i.e., to immediately surrounding tissue but is rather applied over a comparatively large surface area so as not to affect the surrounding tissue adversely.

5 Claims, 10 Drawing Figures

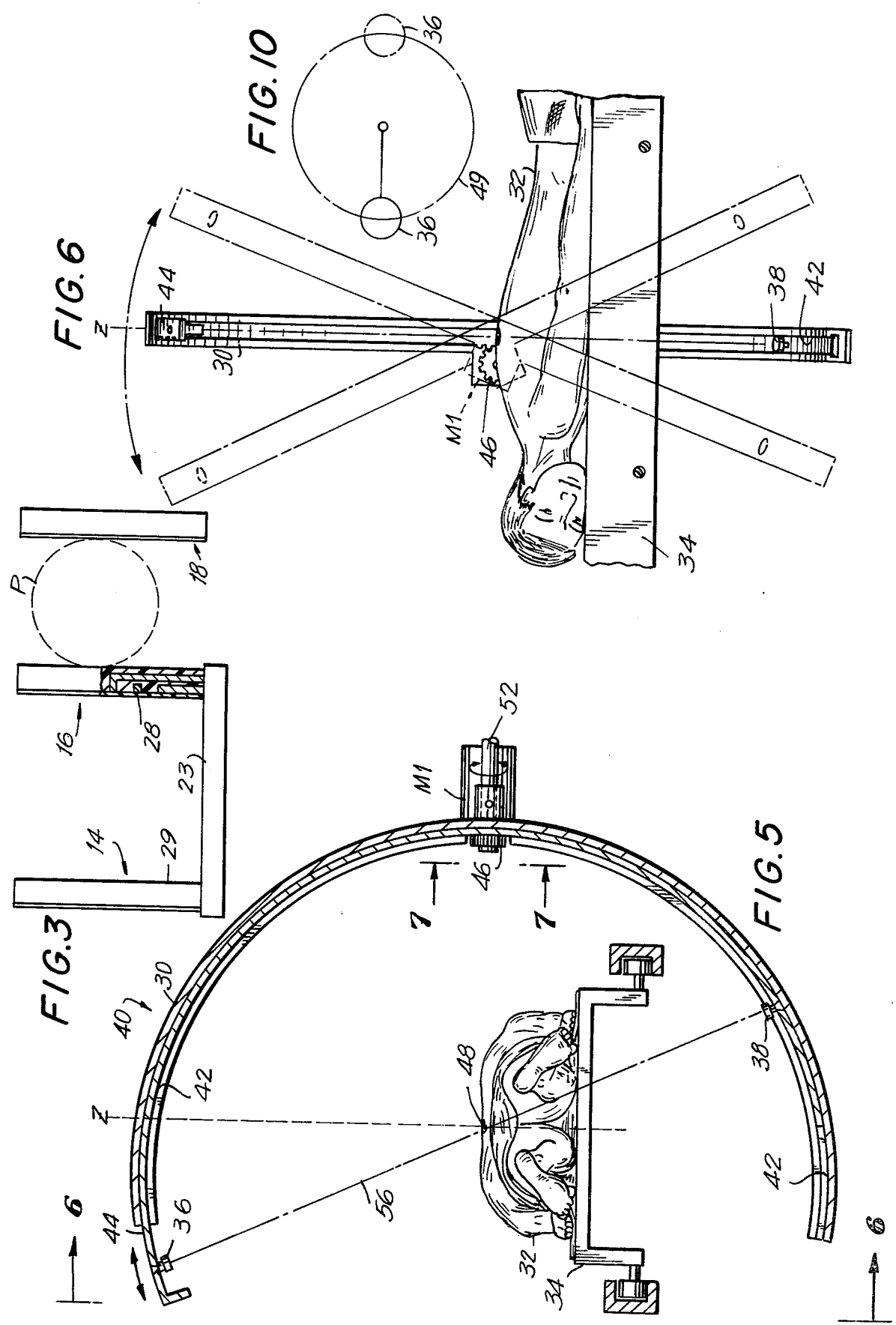

RADIO FREQUENCY, ELECTROMAGNETIC RADIATION DEVICE HAVING ORBITAL MOUNT

RELATED APPLICATIONS

This application is a continuation-in-part of LeVeen application Ser. No. 643,661 filed Dec. 23, 1975, now U.S. Pat. No. 3,991,770, granted Nov. 16, 1976 which is in turn a continuation-in-part of LeVeen application Ser. No. 595,094 filed July 11, 1975 (now abandoned), the last named being in turn a continuation-in-part of LeVeen application Ser. No. 436,102 filed Jan. 24, 1974 (now abandoned), and is related to LeVeen application Ser. No. 595,095 filed July 11, 1975. The benefit of the aforecited applications as to common subject matter is herewith claimed. It should also be noted that the disclosures of the related applications are incorporated herein by reference.

BACKGROUND, OBJECTS AND SUMMARY OF THE INVENTION

This invention relates to the treatment of tumors in animal hosts, such as in human beings, and in particular provides a technique for destroying tumors without injury to surrounding normal tissue.

It is a fundamental object of the present invention to provide a suitable method and apparatus that can be applied to the heat treatment of tumors at varied locations within the body of the animal host, particularly when that host is a human being, such that the treatment can be completely monitored, that is, the change in the tumor can be observed in real time and corrections taken if required. Moreover, another primary object is to enable extremely efficient coupling of RF energy to a patient's body such that there is not significant heat absorption in the fatty tissues, but rather only at the site of the tumor or cancer itself.

Reference to the aforesaid patent applications, particularly application Ser. Nos. 643,661 and 595,094, will make clear that tumors have been destroyed in humans by heating the portion of the body containing the tumor so that the temperature of the tumor is raised to a point at which it becomes necrosed, that is, at or above a temperature of about 50° C. The underlying principle for achieving this objective is the fact that when the tumor containing portion of the body is heated by applied radio frequency electromagnetic radiation, the tumor is heated differentially, i.e., to a greater extent than normal tissue such that the temperature of the normal surrounding tissue can be kept below 40° C.

The basic reason that the technique described in the aforesaid applications has been effective is that the blood flow through carcinomas and other neoplasms is sluggish. While tumors possess an angiogenetic factor which initiates the formation of new blood vessels, these however are capillaries which offer great resistance to blood flow.

From experiments which have been conducted, it turns out that when the tumor or malignancy is especially deep-seated and difficult to affect with RF energy because of surrounding fatty tissue, the radiation sometimes has to be of such intensity and to be applied for such an extended period of time that, although the desired differential heating of the tumor is accomplished, yet the surrounding normal tissue is unavoidably thermally damaged.

However, it has been discovered that successful treatment can be effected in the aforesaid difficult cases such that excessive heating or thermal damage to the surrounding tissue is avoided by providing apparatus for moving the applicator plates or discs in an orbital manner whereby the tumor to be treated always lies on an axis between the applicator plates. As a result, the radio frequency energy is focused or concentrated on the tumor but because of the orbital movement of the applicators the energy is not being continuously applied to the same confined area within the patient's body, that is, to the tissue and organs immediately surrounding the tumor. Instead, the applied energy is swept over a comparatively large core or volume so as not to affect the surrounding body tissue adversely.

Essentially then, the present invention improves upon apparatus and techniques previously developed by the present inventor. In those previously developed techniques which can be appreciated by reference to the previously recited patent applications, it was generally understood that a variety of kinds of applicators could be applied to the patient's body if desired. These applicators are, of course, normally insulated and are placed on opposite sides of the portion of the body near the location of the tumor. As described in those applications, radio frequency energy is applied to the applicators with the result of localized heating in the tumor differentially higher than that of the surrounding normal tissue, heating being continued for a duration and at an intensity sufficient to cause necrosis of the tumor by reason of reaching a temperature therein of about 50° C. However, the heating, in most of the cases involving apparatus in accordance with the previous inventions, has been insufficient to raise the temperature of the surrounding normal tissue so that thermal damage is caused.

In the normal course of operating the radio frequency equipment for the purpose of destroying tumors, differential thermometry is provided so that the difference in temperature between the given tumor and the surrounding tissue can be monitored. This is generally done with non-metallic thermometers having nonelectrolyte fluid such as liquid alcohol filled thermometers. Temperatures as high as 60° C. can be achieved within the tumor while the surrounding normal tissue is heated only to the vicinity of 40° C. under the assumption that about 500 watts of energy at a preferred frequency of 13.56 MHz is employed.

It has been found to be generally desirable to employ radio frequencies which are as low as permissible in order to enhance absorption of energy by the tissues. As a result, the lowest frequencies permitted by the FCC are preferable. The practical frequency range to produce the requisite internal heating for treatment of tumors in accordance with the present invention is from about 100 KHz to about 200 MHz. Since the longer wave lengths are both more effective for heating purposes and are less likely to cause damage by scattering and the like, the preference is distinctly for the longer wave lengths. As previously indicated, the preferred frequency for tumor treatment is 13.56 MHz because this is the longest wave length presently permitted by law.

The apparatus of the previously cited applications have generally utilized powers in the range of 200 to 500 watts. In the present improvement, the power range has been increased to the range of 2 to 4 kilowatts, such range being suitable inasmuch as the applicators are located for the purposes of orbital movement so that the same volumes of tissue will not be exposed to radiation and consequently the actual power conveyed to the patient's body is of the order of 200 to 300 watts. The normal times of exposure to radiation are typically from 10 to 20 minutes, although greater or shorter periods can be employed depending on the size and location of the tumor.

Accordingly, it is a primary object of the present invention to effectuate or carry out treatment on difficult and deep-seated tumors that require long exposure times to radiation and to successfully obviate the problem of excessive heating of the surrounding tissue.

In accordance with the primary feature of the present improvement or invention, the radio frequency, electromagnetic radiation equipment or apparatus is arranged so that the applicators to which a radio frequency generator and amplifier are connected are so arranged that they can be located on opposite sides of the patient's body and along a central axis and to be moved in such a way that the radio frequency energy will be directed at the tumor location but the applicators or plates will be orbited around the central axis so that a given surrounding volume of tissue is not continuously exposed to the RF radiation. Instead, by reason of the orbital movement, only a limited surface area or volume adjacent the tumor is exposed for a predetermined short period of time, the applicator moving continuously away from that given area in its orbital motion.

The above-indicated orbital motion or movement is provided by concurrent application of driving power to a yoke member such that its resultant direction of movement is a combination of movements due to individual force vectors. More specifically, the yoke member is rotated part way about a horizontal axis and concurrently therewith the yoke member is moved in a reciprocating manner, in the plane of rotation. As a result, the combination of movements defines a circular orbital path.

Additionally, the yoke member can be raised or lowered depending upon the location of a given tumor, that is to say, it is elevated from the floor, or table, reference plane a more or less amount. In other words, the yoke member can be adjusted above a horizontal reference plane depending on whether the tumor is toward the anterior or posterior side or part of the patient's body. As far as transverse (X) and longitudinal (Y) coordinates are concerned, the table on which the patient rests can be moved in these directions so as to insure proper alignment of the tumor on the desired axis.

A further fundamental feature of the present invention resides in the concept of combining the tumor treating apparatus with a body scanner device or apparatus. For example, such latter equipment has been described in U.S. Pat. No. 3,839,641 in which there is described a method of an apparatus for the radio nuclide imaging of the whole body of a patient using an unmodified scintillation camera permitting a patient to be continuously moved under or over the stationary camera along predetermined axes. Such a system enables judicious enlargement or enhancement of the image of a particular area of the body, such as an area in which a tumor may be located.

It is well known that there is a detectable amount of radiation from the human body and that tumors radiate more energy than normal tissues because they possess higher base temperatures. In accordance with this knowledge it is possible, using a body scanner, to continuously monitor the condition of a tumor that is being treated by the radio frequency apparatus of the present invention.

As the process of heat treating the tumor proceeds it will be manifest that the absorption of radiation from the RF apparatus will permit an excellent display of the tumor condition as it is being treated, since the absorbed energy will result in a much higher differential temperature in the tumor and consequently a much greater degree of radiation therefrom, compared to normal tissue, when the RF equipment is turned off and the radio active material which has been ingested by the patient is permitted to be monitored by the body scanner.

Other and further objects, advantages and features of the present invention will be understood by reference to the following specification in conjunction with the annexed drawing, wherein like parts have been given like numbers.

BRIEF DESCRIPTION OF DRAWINGS

FIG. 3 is an elevational view of the three applicators previously seen in FIG. 1;

FIG. 5 is a view taken on the line 5—5 in FIG. 4;

FIG. 6 is a view taken on the line 6—6 in FIG. 5;

FIG. 10 is a view of the orbital movement of the applicators due to the combined movements of the yoke assembly.

DESCRIPTION OF PREFERRED EMBODIMENT

Figure 1:
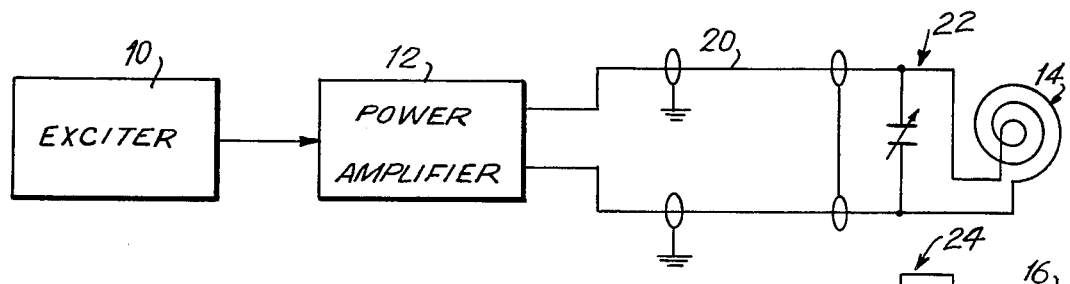
FIG. 1 is a block diagram illustrating apparatus as described in applicant's previous applications and constituting part of the means for carrying out the technique of the invention described therein.
Figure 2:
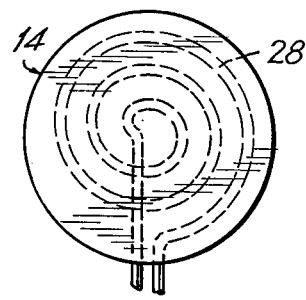
FIG. 2 is an end view of one of the applicators in accordance with the previous inventions.

Referring now to FIGS. 1 and 2, an arrangement of apparatus as described in the aforesaid related applications Ser. Nos. 643,661 and 595,094, includes an exciter 10, a power amplifier 12 and three applicators 14, 16 and 18. The applicator 14 is directly connected by means of coaxial cable 20 to the power amplifier 12.

It has been found that heating in accordance with the previous invention could be obtained where each of the applicator structures as in applicators 14, 16 and 18 is basically an inductance. Moreover, the particular configuration or arrangement of applicators as seen in FIG. 1 was found to be preferred in achieving optimum distribution of the electromagnetic field so as to confine the electromagnetic energy to the desired tumor region for localized heating of the tumor.

Briefly described, the complete apparatus of the previous invention involves a primary circuit 22 in which applicator 14 is connected and two secondary circuits 24 and 26 in which applicators 16 and 18 are connected.

The primary circuit 22, or what may be termed a driver section, sets up the required electromagnetic field. Its input impedances is approximately 50 ohms when adjustments are properly made and resonance is attained. The power output from amplifier 12, which is preferably of the order of 2-4 kilowatts, is delivered to the applicator 14. The secondary circuit 24 has its applicator 16 in the same housing 23 (FIG. 3) as the applicator 14 of the driver section. This secondary circuit is sometimes referred to as a focusing section since it transmits or focuses the RF energy in one direction to the adjacent space. The third circuit, that is, the other secondary circuit 26 is termed a reflector section and is located in the path of the transmitted RF energy. As will be especially seen in FIG. 3, the patient's body or a portion thereof P is disposed between the applicator 16 and applicator 18. The reflector section reflects energy back into the region between the reflector and focuser, that is, in the region to be treated, thereby promoting efficient heating of the tumor or the like within the energy field. The typical distance between the applicators 16 and 18 may be adjusted from 5 to 15 inches. Each of the individual sections, that is, each of the secondary circuits, as well as the primary circuit, is adjusted by manually tuning variable capacitors in the respective circuits.

Each of the applicators 14, 16 and 18 includes a pancake type coil 28 (FIG. 2) which is in the form of a planar spiral of flat silver-plated copper having three turns from the inner to the outer end. Each of the coils 28 is housed in a circular polytetrafluoroethylene (PTFE) disc 29, which is grooved appropriately to receive its associated spiral coil 28, with the connections of each spiral coil extending from the disc 29 for connection to its associated capacitor.

It should be noted that the present invention advantageously exploits the basic and preferred concept of inductive coupling between applicators for efficient distribution of the RF energy and consequent efficient coupling to the patient's body. Moreover, the fundamental improvement resides in providing for ready and adjustable movement of such applicators where difficulty with thermal damage to surrounding tissue is encountered. It turns out that inductive coupling for this and other purposes is superior in that a greater degree of conductivity results within the tumor tissue because such tissue is salt containing. In other words, inductive coupling results in coupling a greater degree or amount of energy to the tumor tissue when compared with capacitive coupling at equal power levels inasmuch as with capacitive coupling closer intimate contact must be had with the skin of the patient and it occurs that much greater losses result in fatty or subcutaneous tissues. However, it will be understood that capacitive coupling can be successfully employed according to which applicators are placed firmly in an intimate contact with the surface of the body portion under treatment and the affected body portion serves as the dielectric.

Referring now to FIGS. 4-8, there is shown the apparatus in accordance with the present invention for efficaciously treating a substantial tumor within the body of a patient, while avoiding serious thermal damage to surrounding tissue. Such apparatus comprises a C-shaped yoke member 30 which partly surrounds the body 32 of a patient situated on a movable table 34. Yoke member 30 carries a pair of applicator assemblies 36 and 38, one of which may include the applicators 14 and 16, and the other the single applicator 18. The applicator 14 is connected to the RF supply, that is, to the power amplifier 12 as previously described.

The applicator assemblies 36 and 38 are adapted to supply the required electromagnetic energy to the tumor 40 once that tumor has been located with reference to the coordinate axes X, Y, and Z as indicated. Such location can be accomplished by means of a conventional X-ray machine. However, preferably this is done by a body scanner device of the type described in U.S. Pat. No. 3,839,641. Moreover, the tumor treating apparatus 40 can be placed under the control of the body scanner device as will be explained hereinafter for complete monitoring of the heat treatment process and of the effects being had on the tumor under treatment.

The yoke structure 30 is normally so positioned that the applicator assemblies 36 and 38 lie on a reference axis also designated as the Z or vertical axis of the coordinate system, whereas the X and Y axes define a plane in which the movable table 34 lies, such plane constituting an important plane of reference in connection with the use of the present invention in combination with the body scanner device or system to be described.

The C-shaped yoke member 30 includes an arcuate track 42 formed at the inner side, and a movable rack 44 is fitted to the track. The rack is engaged by a pinion gear 46 which is driven by a reversible motor connected to a gear reduction drive, such that the rack, and hence the two applicator assemblies 36 and 38, can be shifted from their normal, reference axis orientation either clockwise or counterwise in accordance with manual or automatic selection of motor direction.

For treatment of a centrally located tumor 48, the normal orientation of the table 34 relative to the apparatus 40 will insure that the applicators 36 and 38 are appropriately disposed, i.e. they are suitably located for the desired treatment on the reference or vertical axis (Z). However, in accordance with the principles of the present invention, the applicator assemblies 36 and 38 are to be swung in an orbital manner; that is to say, to be moved as depicted in FIG. 10 along a circular orbit 49 having a selected radius r.

Figure 11:
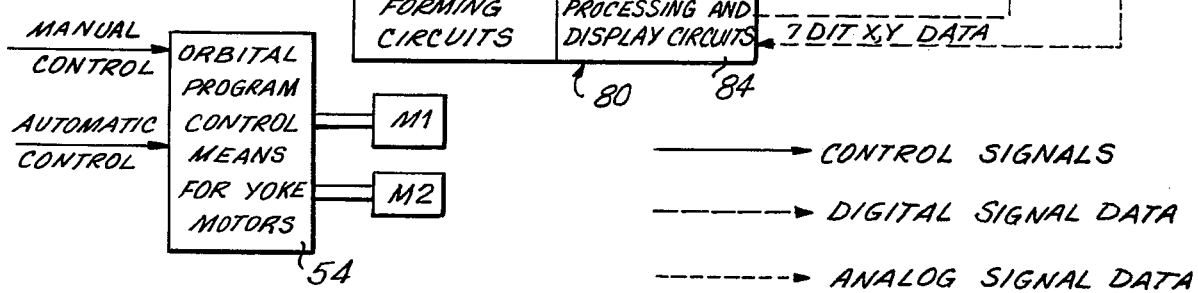

In order to achieve the required orbit, another reversible motor M2 is provided which is likewise connected with a gear reduction mechanism 50 and which is, in turn, connected to the shaft 52 so as to turn the entire yoke structure away from the ZY plane in either direction. This rotational movement is correlated with the aforedescribed movement of rack 44 substantially pari passu so that the orbit 49 results. The correlation is effected by a programmed control means 54 (FIG. 11) which directs signals, under feedback control, of appropriate magnitude and polarity to the motors M1 and M2. The program is normally manually initiated but may be controlled automatically at the direction of a body scanner device or system to be described.

In the above described manner, that is, by reason of the aforesaid orbital movement of the pair of applicator assemblies 36 and 38, the body of the patient or, more precisely, the volume surrounding or adjacent the tumor undergoing treatment, is not continuously exposed to the electromagnetic radiation from applicator assemblies 36 and 38. Thus, although the applicator assemblies are always focused or directed along a predetermined axis on which the tumor lies, they are being moved such that they reach an axis 56 (see in broken lines) in one direction and an equally distant axis 58 in the opposite direction. It will be appreciated that the applicator assemblies sweep over a relatively large surface area of an imaginary sphere (and hence affect a corresponding volume within the patient's body). Accordingly, the radiation is not being continuously imposed upon or absorbed by the same tissue surrounding the tumor for the entire duration that the electromagnetic energy is being absorbed by the tumor.

Figure 4:
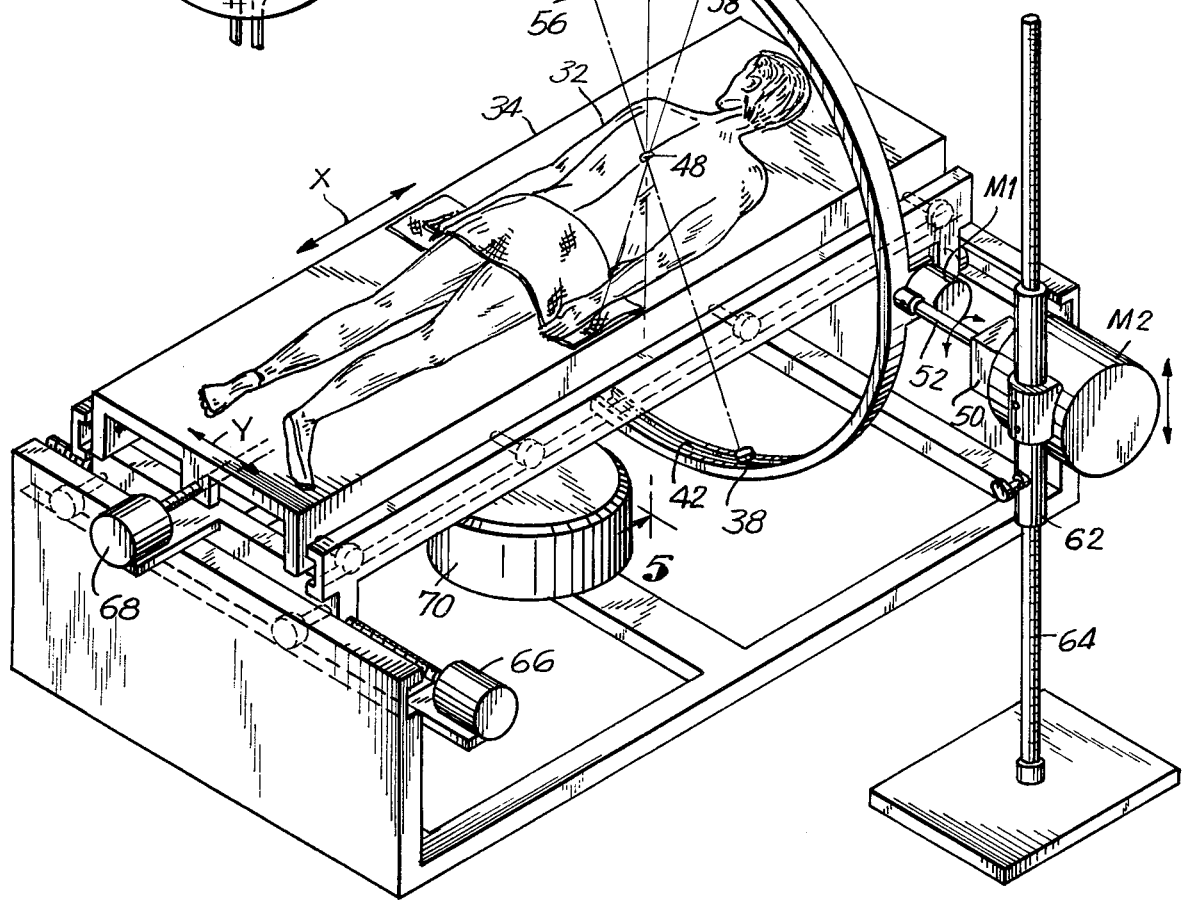
FIG. 4 is a perspective view of a complete system in accordance with the present invention, illustrating the radio frequency treating apparatus, which includes means for enabling orbital movement of the applicators; and also illustrating a movable table and a body scanner device.
Figure 7:
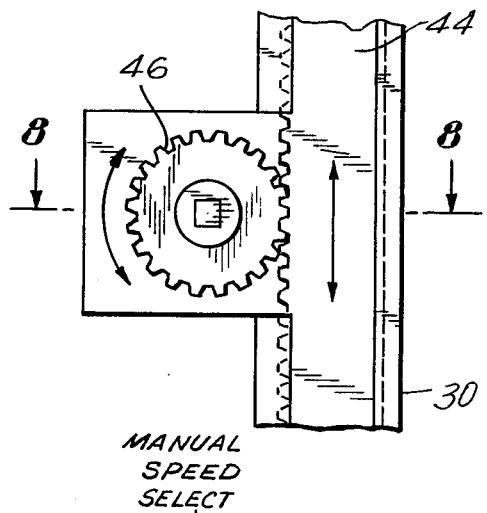
FIG. 7 is a fragmentary view of the drive mechanism for the yoke-applicator assembly, the view being taken on line 7—7 in FIG. 5.
Figure 8:
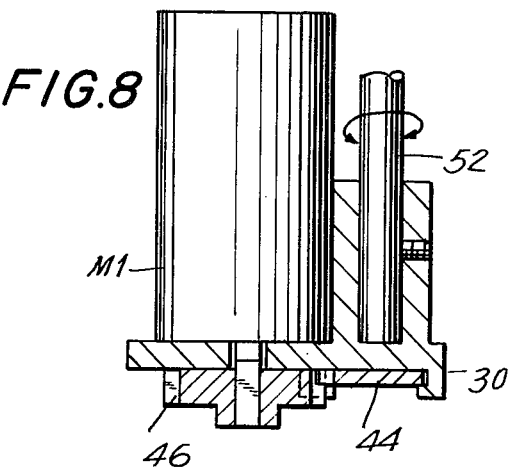
FIG. 8 is a fragmentary view of another part of the drive mechanism, taken on the line 8—8 of FIG. 7.

Should the tumor lie in a slightly different location from the tumor 48 depicted in FIG. 4 such as, for example, should it lie at a slightly higher or lower elevation, a suitable height adjustment is made by means of an adjustable clamp 62 on a post 64 which supports the yoke 30. Accordingly, in such case the entire yoke assembly would be suitably elevated by this means. Also, should the tumor be located to either right or left of the location 48, then the table 34 would be simply shifted transversely by operation of motor 66, under the assumption that the tumor lies at the same longitudinal point within the patient's body. If the longitudinal location differed from that shown, table 34 would be suitably moved by operation of motor 68. The transverse and longitudinal movements of table 34 are provided by either manually operated means or by automatic control.

It should be noted that if it should be preferable that the table 34 be moved in the vertical direction so as to accomplish the desired change in elevation, then an additional motor (not shown) can be provided for this purpose.

For much increased efficiency in locating a particular tumor within the patient's body and also for completely monitoring the tumor destroying process or operation, advantage is taken of a recent development referred to as a body scanner device or system. The details of such a device can be appreciated by reference to the U.S. patent already cited. In such a system, a scintillation camera 70 is provided beneath the movable table 34 and the motors 66 and 68 are controlled by the body scanner system.

Several significant results obtainable by a whole body scanning device are that the scintillation camera used (sometimes called a Dynacamera) enables an object field to be digitized in the image presentation such that each point in the image can be represented by two seven bit binary numbers. These numbers can be suitably processed and stored and can be translated when required into analog signals so as eventually to display either a normal image or a whole body scan. Furthermore, the image or images obtained can be displayed on the faces of a persistent oscilloscope for monitoring and on another oscilloscope from which a photographic image can be produced by integration of all events occurring during exposure.

Another important or significant aspect of the body scanner device or system is that the aforesaid analog signals can be used for all regular Dynacamera processing operations such as image rotation, area of interest selection, generation of count profiles by the data processor and the production of a photographic image from the display oscilloscope.

In connection with the treatment of tumors in accordance with present invention, the ability to focus in on the area of the tumor is of crucial importance. Thus, the "area of interest selection" feature in accordance with the body scanner system permits a surgeon or other medical practitioner to carefully locate the tumor to be treated and, if desired, to completely monitor the procedure of destroying the tumor. Thus the present invention uniquely capitalizes on the capability of the body scanner device for communicating with and directing the tumor therapy apparatus in performing its function.

Figure 9:
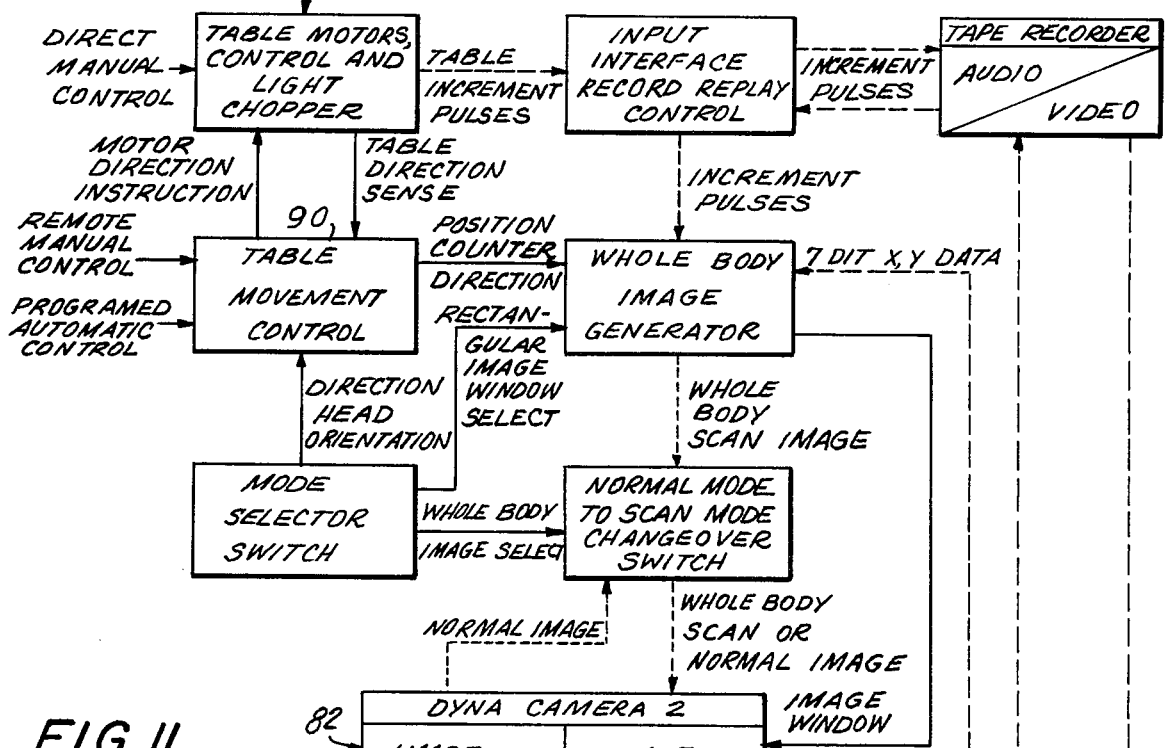
FIG. 9 is a block diagram illustrating the electronic aspects and particularly the controls on the body scanner device.

Referring to FIG. 9, a block diagram is there shown which depicts the electronic inter-relationships among the tumor treating apparatus 40, the movable table 34, the scintillation camera 70 and the associated data processing equipment. The scintillation camera or Dynacamera, circuitry is generally denoted by numeral 80 and is divided into two basic parts, the image forming section 82 and the image processing section 84. The image forming section 82 generates the previously noted two seven bit binary numbers representing a scintillation event at coordinates $x_i$ and $y_j$, respectively. These binary numbers are available in parallel form from a holding register in the Dynacamera both during recording and during replay from tape. The digital $x_i, y_j$ position is subsequently converted to two analog position signals.

The circuit schematic described makes it possible to externally generate the sums $X_a + x_i$ and $Y_b + y_j$ digitally to form $X_i Y_j$ and then to convert these analog signals whose sense and magnitude match those generated within the scintillation camera. The signals are then injected into the scintillation camera in the place of the $x_i, y_j$ analog signals. Hence the processing circuitry operates on analog signals of similar magnitude but carrying more information, potentially that of a whole body image when the full $X_i Y_j$ matrix is displayed on the oscilloscope or when a whole body count profile is resolved into a hundred points displayed on the data processor.

The data processor is a modified 100 channel analyzer which displays count profiles taken along the x axis of the image display oscilloscope. Rotation of the image relative to this axis enable various profiles to be generated since the multi-channel analyzer operates on the X component of the analog position signal after rotation. The X component of any displayed image is divided into one hundred intervals and a profile of counts per interval is then displayed on the processor oscilloscope. In clinical terms the longitudinal count profile of a whole body scan may be examined at any level as a transverse count profile. Therefore two overlapping organs in longitudinal profile for example, liver and spleen, which are seen as a single integrated peak, may be differentiated in transverse profile and individual organ activity defined by integration of the two peaks.

Because of the inherent ability of the body scanning device or system to operate in the manner described, the area of interest such as a tumor within an organ, for example, the liver, can be focussed in on, with suitable enlargement of the tumor image. Then, very precise orientation can be obtained because of the table movement control 90. That is to say, the table moves automatically relative to the radio frequency tumor treating apparatus 40 such that the located tumor is placed on the Z or vertical reference axis. Accordingly, there is automatic achievement, because of the relationship with the body scanner system, of the required positioning for the applicators. Thus, the applicators are properly aligned with the tumor for treatment in the manner already described by which the desired results of avoiding thermal damage to surrounding tissue is effected.

Subsequent to the control of the exact positioning desired for the tumor as displayed, the automatic program for the orbital movement of the yoke and applicators as described is then effectuated.

What has been disclosed is a unique method and apparatus or system for treating tumors whereby efficient location and monitoring of a tumor to be treated by radio frequency, electromagnetic energy can be achieved by reason of the combination of such apparatus with a whole body scanning device or system. In addition, the method and apparatus of the present invention overcomes a difficult problem in that it avoid excessive heating a consequent thermal damage to normal tissue surrounding a tumor to be treated.

Although a specific embodiment has been described in detail for the present invention variations thereon will be apparent. Thus, although the complete equipment is embodied as seen in FIG. 4 so as to constitute a physically integrated unit, the tumor therapy apparatus can and does stand alone, and the information relating to tumor location can be transferred from the available tape recording onto a punched card or other means so as to control a distant tumor therapy apparatus.

What is claimed is:

1. Apparatus for treating tumors and the like in an animal host, comprising:
a yoke, an elongated member slidably mounted on said yoke for movement therealong on an arcuate path, a pair of radio frequency applicators mounted on said slidable member fixed in diametrically spaced relationship and directed toward each other, said applicators being adapted to be connected to a source of radio frequency electromagnetic power to set up a radio frequency electromagnetic field therebetween, means for moving said slidable member through said arcuate path with said applicators in said fixed spaced relationship to each other such that said applicators move through an arcuate path about an axis, and means for rotating said yoke whereby said applicators move through an arcuate path about a second axis intersecting said first named axis at a point at which a said tumor in an animal host is locatable.

2. Apparatus as defined in claim 1, in which said first named means includes rack and pinion means.

3. Apparatus as defined in claim 1 further comprising a body scanner means including a scintillation camera positioned relative to said intersecting point for registering scintillation events arising from the presence of a radio nuclide in the host located at said point and a movable table for positioning an animal host at said intersecting point whereby the location of a tumor in said animal can be detected by said scanner means and can be positioned at said intersecting point.

4. Apparatus as defined in claim 3 in which said body scanner means further includes a scintillation detector and a data processor, said scintillation camera representing a scintillation event as a first set of coordinates in terms of a first set of signals, motor means for providing relative movement along both the x and y axes between said scintillation detector and said movable table, means for indicating relative movement between said table and said scintillation detector and for producing a signal in response thereto, and electronic means coupled to said scintillation detector to said data processor and to said movement indicating means for controlling said motor means.

5. Apparatus as defined in claim 4, further comprising means for focusing said body scanner means so as to produce an enlarged image of an area of interest including a tumor;
and means for automatically positioning the movable table in a proper orientation for application of said radio frequency energy by said applicators when said body scanner has focussed on said area of interest.

* * * * *